(12) United States Patent
Ihn et al.

(10) Patent No.: US 7,937,248 B2
(45) Date of Patent: May 3, 2011

(54) VIRTUAL TIME REVERSAL ACOUSTICS FOR STRUCTURAL HEALTH MONITORING

(75) Inventors: Jeong-Beom Ihn, Bellevue, WA (US); James Patrick Dunne, Ballwin, MO (US)

(73) Assignee: The Boeing Company, Chicago, IL (US)

( * ) Notice: Subject to any disclaimer, the term of this patent is extended or adjusted under 35 U.S.C. 154(b) by 851 days.

(21) Appl. No.: 11/861,056

(22) Filed: Sep. 25, 2007

(65) Prior Publication Data

US 2009/0083004 A1 Mar. 26, 2009

(51) Int. Cl.
*G06F 17/50* (2006.01)
(52) U.S. Cl. .................. 703/1; 702/36; 702/35
(58) Field of Classification Search ........ 703/1; 702/35, 702/36
See application file for complete search history.

(56) References Cited

U.S. PATENT DOCUMENTS 6,006,163 A * 12/1999 Lichtenwalner et al. ....... 702/36
2008/0319692 A1 12/2008 Davis et al.

OTHER PUBLICATIONS

Leutenegger et al. "Non-Destructive Testing of Tubes Using a Time Reverse Numerical Simulation (TRNS) Method" Elsevier 2004. See IDS dated Feb. 17, 2009 NPL reference #2.*

Wang et al., "A synthetic time-reversal imaging method for structural health monitoring", Institute of Physics Publishing, Smarter Materials and Structures 13 (2004), U.K., pp. 415-423.
Leutenegger et al., "Detection of defects in cylindrical structures using a time reverse method and a finite-difference approach", May 2002, pp. 721-725, vol. 40, Issues 1-8, Ultrasonics.
Leutenegger et al., "Non-destructive testing of tubes using a time reverse numerical simulation (TRNS) method", May 2004, pp. 811-822, vol. 41, Issue 10, Ultrasonics.
USPTO office action for U.S. Appl. No. 11/840,427 dated Nov. 4, 2009.
USPTO office action for U.S. Appl. No. 12/851,408 dated Sep. 23, 2010.

* cited by examiner

*Primary Examiner* — Kamini S Shah
*Assistant Examiner* — Saif A Alhija
(74) *Attorney, Agent, or Firm* — Yee & Associates, P.C.; John A. Lepore

(57) ABSTRACT

A method, apparatus, and computer program product for monitoring structures using virtual time reversal signal processing. In one embodiment, a signal having a frequency range is sent into a structure in a vehicle from a fixed transmitter to form an original transmitted signal. A response to the original transmitted signal is received at a fixed sensor associated with the structure to form a received response. The received response is reversed. The reversed response is processed using a transfer function to simulate propagation of the reversed response from the fixed sensor to the fixed transmitter to form a simulated time reversed response. The simulated time reversed response is a simulation of a response of the fixed transmitter to receiving the reversed response from the fixed sensor. The simulated time reversed response is analyzed to monitor for anomalies associated with the structure.

25 Claims, 5 Drawing Sheets

VIRTUAL TIME REVERSAL ACOUSTICS FOR STRUCTURAL HEALTH MONITORING

The present disclosure is related to the following applications entitled, Method and Apparatus for Modeling Responses of a Material to Various Inputs, Jeong-Beom Ihn, Ser. No. 11/840,427, filed on Aug. 17, 2007; assigned to a common assignee, and incorporated herein by reference.

BACKGROUND INFORMATION

1. Field

The present disclosure relates generally to processing data, in particular, to generating simulated responses of a material to input. Still more particularly, the present disclosure relates to a method, apparatus, and computer usable program code for using virtual time reversal acoustics for structural health monitoring.

2. Background

Structural health monitoring techniques have been developed and used to monitor materials and structures. These techniques often build or incorporate the health monitoring systems directly into structures. These health monitoring systems may be used to determine whether changes have occurred over time to the structures and materials associated with the structure. For example, sudden changes in environments, such as electromagnetic effects, mechanical stresses, and other environmental effects may affect the integrity of various materials and structures over time. By having health monitoring systems built in to or associated with the structures to monitor the structures during use, appropriate measures and responses may be taken to prevent anomalies and failures and may prolong the life span of these structures.

A structural health monitoring system is typically implemented using a transmitter and a sensor configuration to transmit waveforms at various frequency ranges to an array of transducers and acquire data from the transducers' responses. Thus, a transducer may sometimes function both as a transmitter and a sensor.

An optimal waveform cannot be determined ahead of time because of the lack of information. As a result, a large number of input waveforms having different frequency ranges are used. Large amounts of data are recorded from the responses to prevent missing any information that may be needed. The need to use input waveforms or signals at different frequencies occurs because many parameters are present for optimization. For examples, these parameters include driving frequency, time duration, a number of cycles, window function for amplitude modulation, and other factors.

Time reversal acoustics is a method for focusing and analyzing waves for structural health monitoring. Time reversal acoustics has been used in medical imaging and recently introduced to structural health monitoring communities to identify an anomaly, such as, a tumor or damage to a structure. However, currently, this time reversal method requires sophisticated hardware setup and/or additional steps of actually time reversing and resending the transducer's response.

In other words, current time reversal acoustics involve sending a signal through a structure or medium using a transmitter. A sensor receives the response of the structure or medium to the transmitted signal. The sensor time reverses the received response and sends the time reversed response as a transmitted signal back to the original transmitter. The original transmitter receives the time-reversed transmitted signal and then performs run time reversal analysis on this time reversed received response.

The current method requires that a location from which a response to a signal is required, a transmitter or other device capable of receiving and transmitting the time-reversed signal is necessary. This requires additional hardware and collection of additional data sets. In addition, if the structural health monitoring is being performed on an array of transducers, a data set is collected for each path in the array of transducers. For example, if the array of transducers includes 26 transducers, a data set is collected for 26 times 25 (or 650) possible paths. In other words, to perform time reversal analysis on this array, 650 responses will be recorded and then each of the 650 responses are time reversed and sent out as drive signals for use in time reversal analysis.

The re-transmission and collection of the time reversed response requires additional sophisticated hardware and software. In addition, all of the additional re-transmitted time reversed response data collected by the different input signals are saved in the database. Thus, the amount of data collected is large and takes up a considerable amount of space in a structural health monitoring system.

Therefore, it would be desirable to perform time reversal analysis without actually re-transmitting time reversed signals through transducers and other hardware to reduce the amount of hardware required and the amount of data that has to be collected, saved, and/or retransmitted for a structural health monitoring system.

SUMMARY

The different advantageous embodiments provide a method, apparatus, and computer program product for monitoring structures in a vehicle. In one embodiments a signal having a frequency range is sent into a structure in a vehicle from a fixed transmitter to form an original transmitted signal. A response to the original transmitted signal is received at a fixed sensor associated with the structure to form a received response. The received response is reversed. The reversed response is processed using a transfer function to simulate propagation of the reversed response from the fixed sensor to the fixed transmitter to form a simulated time reversed response. The simulated time reversed response is a simulation of a response of the fixed transmitter to receiving the reversed response from the fixed sensor. The simulated time reversed response is analyzed to monitor for anomalies associated with the structure.

In another advantageous embodiment, material is tested using virtual time reversal signal processing. In this embodiment, a signal is sent into the material using a transmitter. The signal has a frequency range that falls within a selected frequency range to form a transmitted signal. An actual response to the transmitted signal is received at a sensor. The actual response is reversed to form a time reversed response. The time reversed response is processed using a functional model. The functional model simulates transmitting the time reversed response back through the material to the transmitter to form a simulated time reversed response. The simulated time reversed response is compared to the actual response to determine if a change has occurred in the material.

In yet another embodiment, a structural health monitoring system has a plurality of components; a set of transmitters physically associated with the plurality of components, a set of sensors physically associated with the plurality of components. The set of transmitters are capable of sending signals into the plurality of components. The set of transmitters are capable of detecting responses to the signals. A transmitter in the set of transmitters sends a signal into a component in the plurality of components. The signal has a frequency range that falls within a selected frequency range to form a transmitted signal. A sensor in the set of sensors receives an actual response to the transmitted signal and generates a simulated time reversed response of the component to the transmitted signal using a functional model. The functional model simulates a response of the component to a time reversed signal to form the simulated time reversed response. An analysis server, wherein the analysis server performs an analysis on the simulated time reversed response to determine if a change has occurred in the material.

Still another embodiment comprises a computer program product on a computer usable medium having computer usable program code for monitoring structures using virtual time reversal signal processing. Computer usable code is present to send a signal having a frequency range into a structure in a vehicle from a fixed transmitter associated with the structure to form an original transmitted response; receive a response to the signal at a fixed sensor associated with the structure to form a received response; reverse the received response to form a reversed response; process the reversed response using a transfer function to simulate propagation of the reversed response from the fixed sensor to the fixed transmitter to form a simulated time reversed response; and perform an analysis on the simulated time reversed response at the original transmitter to monitor for anomalies associated with the structure. The simulated time reversed response is a simulation of a response of the fixed transmitter to receiving the reversed response from the fixed sensor In yet another embodiment, a computer program product comprises a computer usable medium having computer usable program code for testing a material. Computer usable program code is present to send a signal into the material using a transmitter wherein the signal has a frequency range that falls within a selected frequency range to form a transmitted signal; receive an actual response to the transmitted signal at a sensor; reverse the actual response to form a time reversed response; process the time reversed response using a functional model to form a simulated time reversed response; and compare the simulated time reversed response to the original transmitted signal to determine if a change has occurred in the material.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the disclosure are set forth in the appended claims. The disclosure itself, however, as well as a mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
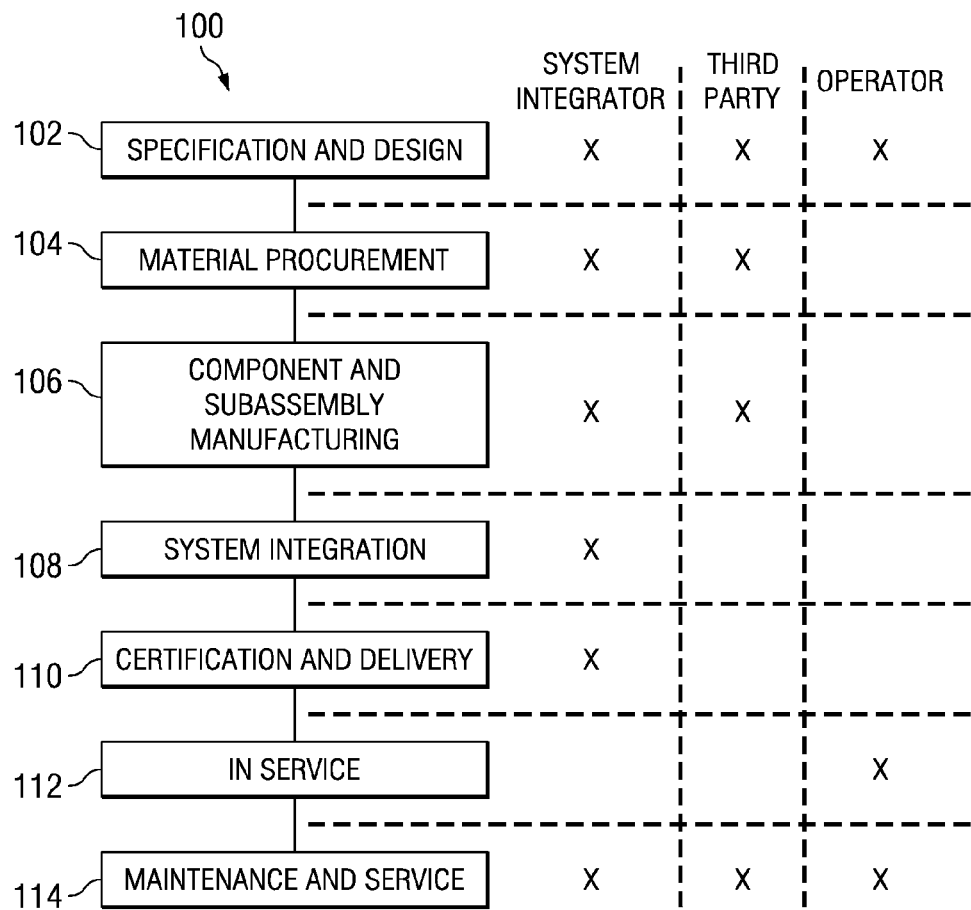
FIG. 1 is a diagram illustrating an aircraft manufacturing and service method in accordance with an advantageous embodiment.
Figure 2:
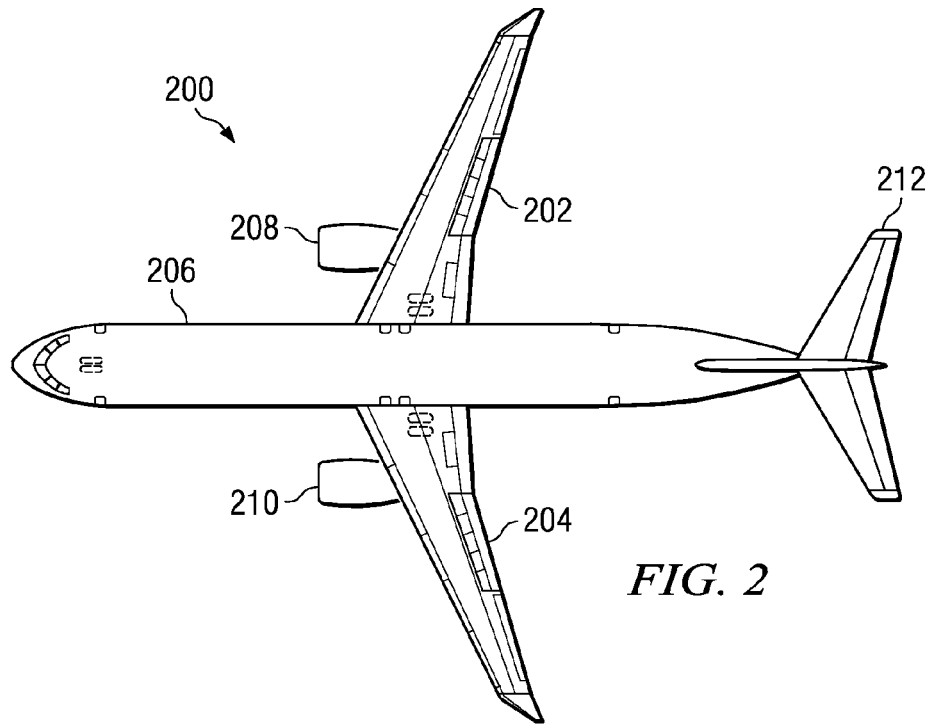
FIG. 2 is a diagram of an aircraft in accordance with an advantageous embodiment.

Referring more particularly to the drawings, embodiments of the disclosure may be described in the context of the aircraft manufacturing and service method as shown in FIG. 1 and the aircraft as shown in FIG. 2. Turning first to FIG. 1, a diagram illustrating an aircraft manufacturing and service method is depicted in accordance with an advantageous embodiment. During pre-production, aircraft manufacturing and service method 100 may include specification and design 102 of aircraft 200 in FIG. 2 and material procurement 104. During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of method 100 may be performed or carried out by a system integrator, a third party, and/or an operator as indicated by the "X" in the grid to the right of the flow diagram of FIG. 1. In these examples, the operator may be a customer. For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 has wings 202 and 204 attached to body 206. Aircraft 200 includes wing mounted engine 208, wing mounted engine 210, and tail 212. Aircraft 200 is produced by aircraft manufacturing and service method 100 in FIG. 1.

Apparatus and methods embodied herein may be employed during any one or more of the stages of production and service method 100 in FIG. 1. For example, components or subassemblies corresponding to component and subassembly manufacturing 106 may be fabricated or manufactured in a manner similar to components or subassemblies produced while aircraft 200 is in service.

Also, one or more apparatus embodiments, method embodiments, or a combination thereof may be utilized during production stages for component and subassembly manufacturing 106 and system integration 108 in FIG. 1, for example, by substantially expediting assembly of or reducing the cost of aircraft 200. Similarly, one or more of apparatus embodiments, method embodiments, or a combination thereof may be utilized one of during different stages, such as component and subassembly manufacturing 106, and system integration 108, in service 112, and/or routine maintenance and service 114 of aircraft 200 in FIG. 2.

Figure 3:
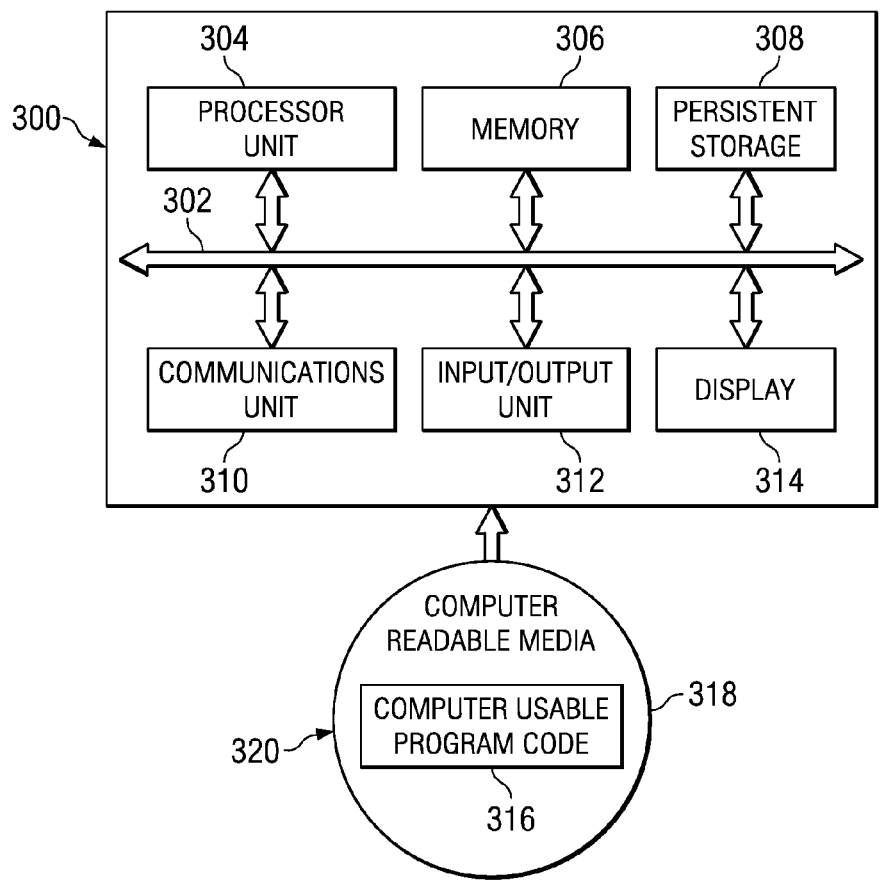
FIG. 3 is a diagram of a data processing system in accordance with an advantageous embodiment.

Turning now to FIG. 3, a diagram of a data processing system is depicted in accordance with an advantageous embodiment. Data processing system 300 may be implemented in any type of computing device. In this example, data processing system 300 is an analysis server for analyzing simulated time reversal responses to monitor structural health and test for anomalies associated with structures.

In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a set of one or more processors or may be a multi-processor core, depending on the particular implementation. Further, processor unit 304 may be implemented using one or more heterogeneous processor systems in which a main processor is present with secondary processors on a single chip. As another illustrative example, processor unit 304 may be a symmetric multiprocessor system containing multiple processors of the same type.

Memory 306, in these examples, may be, for example, a random access memory. Persistent storage 308 may take various forms depending on the particular implementation. For example, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communications links.

Input/output unit 312 allows for input and output of data with other devices that may be connected to data processing system 300. For example, input/output unit 312 may provide a connection for user input through a keyboard and mouse. Further, input/output unit 312 may send output to a printer. Display 314 provides a mechanism to display information to a user.

Instructions for the operating system and applications or programs are located on persistent storage 308. These instructions may be loaded into memory 306 for execution by processor unit 304. The processes of the different embodiments may be performed by processor unit 304 using computer implemented instructions, which may be located in a memory, such as memory 306. These instructions are referred to as computer usable program code or computer readable program code that may be read and executed by a processor in processor unit 304.

The computer readable program code may be embodied on different physical or tangible computer readable media, such as memory 306 or persistent storage 308.

Computer usable program code 316 is located in a functional form on computer readable media 318 and may be loaded onto or transferred to data processing system 300. Computer usable program code 316 and computer readable media 318 form computer program product 320 in these examples. In one example, computer readable media 318 may be, for example, an optical or magnetic disc that is inserted or placed into a drive or other device that is part of persistent storage 308 for transfer onto a storage device, such as a hard drive that is part of persistent storage 308. Computer readable media 318 also may take the form of a persistent storage, such as a hard drive or a flash memory that is connected to data processing system 300.

Alternatively, computer usable program code 316 may be transferred to data processing system 300 from computer readable media 318 through a communications link to communications unit 310 and/or through a connection to input/output unit 312. The communications link and/or the connection may be physical or wireless in the illustrative examples. The computer readable media also may take the form of non-tangible media, such as communications links or wireless transmissions containing the computer readable program code.

The different components illustrated for data processing system 300 are not meant to provide architectural limitations to the manner in which different embodiments may be implemented. The different illustrative embodiments may be implemented in a data processing system including components in addition to or in place of those illustrated for data processing system 300. Other components shown in FIG. 3 can be varied from the illustrative examples shown.

Figure 4:
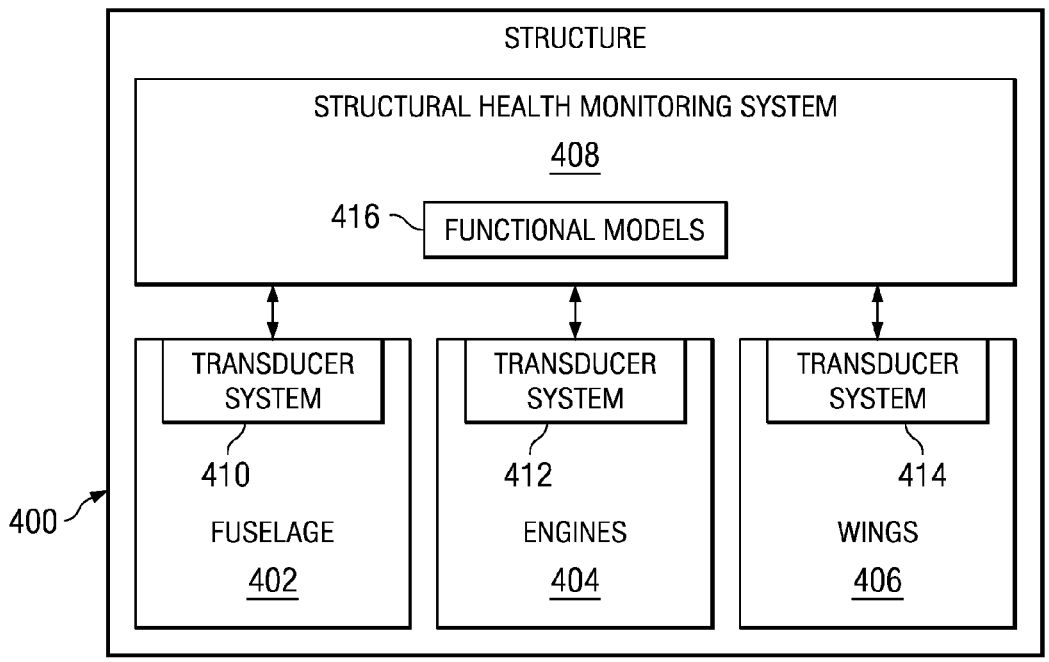
FIG. 4 is a diagram illustrating components used for structural health monitoring in a structure in accordance with an advantageous embodiment.

Turning now to FIG. 4, a diagram illustrating components used for structural health monitoring in a structure are depicted in accordance with an advantageous embodiment. Structure 400 is an example of a structure in which a health monitoring system may be implemented. Structure 400 may take many forms, such as an aircraft, a car, a tank, a ship, a submarine, a spacecraft, a dam, a building, or a bridge.

In this example, structure 400 takes the form of an aircraft. Structure 400 includes fuselage 402, engines 404, and wings 406. Other components also are found in structure 400, but only these depicted ones are presented for purposes of illustrating different features in the different advantageous embodiments.

Structure 400 also includes structural health monitoring system 408, transducer system 410, transducer system 412, and transducer system 414. Although transducers are used for transmitters and sensors in these examples, any type of transmitter, sensor, or device may be used that is capable of sending and detecting signals at the frequencies needed to transmit the signals into a material.

Structural health monitoring system 408 may be implemented in structure 400 using a data processing system, such as data processing system 300 in FIG. 3. Structural health monitoring system 408 may take the form of software, hardware, or a combination of software and hardware. In this example, structural health monitoring system 408 is implemented in software using a data processing system, such as data processing system 300 in FIG. 3.

Transducer systems 410, 412, and 414 are examples of transmitters and sensors that may be implemented in structure 400 to transmit signals and detect responses to those signals. In these examples, the transducers in these systems are "associated" with the particular components in structure 400. A transmitter or sensor, such as those in transducer systems 410, 412, and 414, may be physically associated with the component by being attached to the component or even embedded within the component. In these examples, the transducers are fixed transmitters and fixed sensors that are not moved once they are placed.

In this depicted example, transducer system 410 is a set of one or more transducers that is placed onto or within fuselage 402. Transducer system 410 may be attached to surfaces within fuselage 402 or may be embedded into the materials itself, depending on the particular implementation. The different transducers within transducer system 410 are arranged to be capable of monitoring one or more areas within fuselage 402. These areas may be selected based on different factors, such as identifying areas in which damage may cause an anomalous condition within fuselage 402. In a similar fashion, transducer system 412 is attached to or integrated with components in engines 404. Transducer system 414 also is integrated and configured to collect data from one or more areas in wings 406.

Transducer systems 410, 412, and 414 are controlled by structural health monitoring system 408. Structural health monitoring system 408 may send signals for transmission by these transducer systems. Further, the responses received to these signals are returned to structural health monitoring system 408 for processing. The responses collected from transducer systems 410, 412, and 414 are compared to simulated responses generated by functional models 416.

Functional models 416 contain models that simulate responses for different transducers and receivers for different frequency ranges, in these examples. A functional model may be present for each transmitter and receiver configuration to simulate the response that is detected by a particular sensor when a particular transmitter is used. Thus, a different functional model may be present for the same sensor when a signal is transmitted by different transmitters, in these examples.

Time reversal signal processing is a technique for focusing signals transmitted through a target material. Time reversal signal processing transmits a signal towards a target material. The signal may pass through the material or be reflected off the material to form a response of the material to the signal. The response of the target is a weak emitted signal. The time reversal process reverses the response and retransmits the response through the material. Sending the reversed version of the signal back through the material effectively auto-correlates and focuses the signal. As the process is repeated, the signal becomes more focused on the target material.

Figure 5:
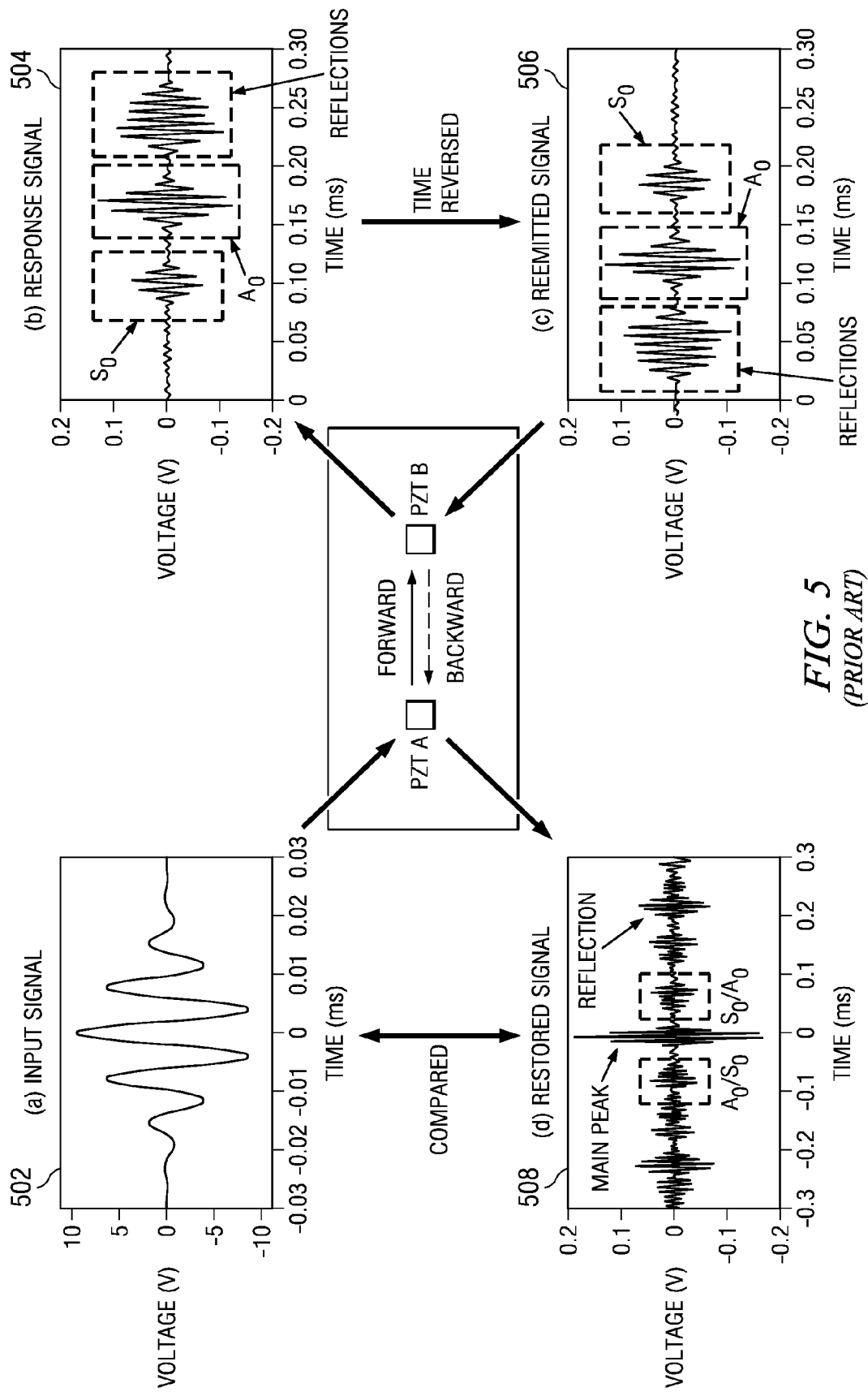
FIG. 5 is a diagram illustrating a conventional time reversal method.

Referring to FIG. 5, a diagram illustrating a conventional time reversal method is shown. Time reversal method 500 is a currently used time reversal process. The process uses a transmitter to send input signal 502 through a material, such as a structure or medium. The material may be, without limitation, structure 400 in FIG. 4.

Input signal 502 is sent through the structure or medium using a transmitter. Input signal 502 contacts the material and then reflects off of the material or moves through the material to generate response signal 504.

A sensor receives response signal 504. Response signal 504 is a response of the structure or medium to the transmitted signal. A data processing system, such as, without limitation, data processing system 300 in FIG. 3, time reverses response signal 504 to form a time reversed signal. The process sends the time reversed signal as a re-emitted or re-transmitted signal, such as reemitted signal 506, back to the original transmitter location. In other words, reemitted signal 506 is a time reversed signal that is sent back to the transmitter that originally sent input signal 502 through the structure or medium to generate response signal 504.

When the original transmitter receives reemitted signal 506, the process uses a data processing system to perform a run time reversal analysis on reemitted signal 506. This process requires that all locations that need to detect response signal 504 also need to have the appropriate hardware and software to generate reemitted signal 506 and re-transmit reemitted signal 506 back to the original transmitter to form restored signal 508. Restored signal 508 is compared to input signal 502 using time reversal analysis to determine if any anomalies or damage to the structure is present.

In this example, only a single transducer is associated with the time reversal method. However, if an array of transducers is associated with the structure or material being tested, monitored, or manufactured, the hardware, data collection, and data transmission requirements can increase exponentially. For example, if an array of transducers includes only three (3) transducers, there would be nine (9) different paths to test. In this example, input signal 502 is sent to each of the transducers along each possible path, for a total of nine input signals. A response signal, such as response signal 504, is generated for each path, for a total of nine response signals. Each of the nine response signals is time reversed and re-transmitted back to the original transmitter. This would require sufficient computing devices and hardware transmitters at each of the three transducer locations to perform the time reversal and re-transmit each of the nine time reversed responses back to the original transmitter for use in structural health monitoring analysis.

Moreover, an array of transducers may include any number of transducers. For example, an array of transducers could include ten, one-hundred, or two hundred transducers. However, to perform time reversal on such a system, when input signal 502 is transmitted to all two hundred transducers, the sensing transducers have to perform time reversal and send a specific drive signal, the time reversed response, back to each individual transmitting transducer. If the array of transducers includes two hundred (200) transducers, the hardware needed to perform time reversal and retransmit time reversed responses back to the original transmitter for analysis could be extremely burdensome, impractical, and cost prohibitive.

For example, if a health monitoring system includes 26 transducers, typically, the process steps through each transducer as the actuator which sends out a drive signal, such as input signal 402 in FIG. 4, to cause each of the other 25 transducers to generate a response signal, such as response signal 504. All 25 responses are different and needed for the time reversal process because each path between the 26 transducers is unique. Even though the input signal is sent by the same transducer, the first transducer, the responses are not the same. So in this example, the first transducer sends out an input signal to cause the other twenty-five transducers to generate twenty-five responses. Then the second transducer sends an input signal to the other 25 transducers to cause the other 25 transducers to generate 25 more responses. The process continues in this manner until each of the 26 actuators sends out an input signal to the other 25 actuators to generate 26 times 25 or 650 responses.

The different advantageous embodiments recognize that in structural health monitoring, it is typical to send input signal 502 out on transmitters and then record response signal 504 on sensors. However, due to the complexity of the hardware requirements and the additional time requirements, it is not typical to process response signal 504 into a time reversed response and then re-transmit the time reversed response to the original transmitter, such as reemitted signal 506, because it is unduly complex and expensive to implement due to the requirements for hardware transmitters and computing devices.

The embodiments recognize that a method for performing time reversal virtually without actually time reversing and identify anomalies with minimal data collection and minimal hardware would be advantageous. Thus, the different advantageous embodiments provide for virtual time reversal acoustics for structural health monitoring by simulating the time reversal response through virtual simulations, rather than using data from actual tests to generate an actual time reversal response for comparison. In other words, rather than using hardware to generate a time reversal response to input for use in structural health monitoring, the different advantageous embodiments utilize a functional model which generates simulated time reversal responses in response to the input.

The different advantageous embodiments provide a method, apparatus, and computer program product for monitoring structures in a vehicle. The structure is a structure associated with the vehicle. The structure may be a structure associated with an aircraft, a car, a tank, a ship, a submarine, a spacecraft, a bridge or any other type of vehicle.

In one embodiment, a signal having a frequency range is sent into a structure in a vehicle from a fixed transmitter to form an original transmitted signal. A response to the original transmitted signal is received at a fixed sensor associated with the structure to form a received response. The received response is reversed. The reversed response is processed using a transfer function to simulate propagation of the reversed response from the fixed sensor to the fixed transmitter to form a simulated time reversed response. The simulated time reversed response is a simulation of a response of the fixed transmitter to receiving the reversed response from the fixed sensor. In other words, the process simulates sending the reversed response from the fixed sensor to the fixed transmitter without actually sending the signal from the sensor to the transmitter.

The simulated time reversed response is analyzed to monitor for anomalies associated with the structure. In this manner, the structure is monitored for anomalies by using time reversal analysis on a simulated time reversed response rather than on an actual time reversed response that would be generated if the sensor actually transmitted the reversed signal from the sensor back through the structure, and then on to the transmitter.

The transfer function is created in one embodiment by sending a wideband signal into the structure. The wideband signal has a selected frequency range that encompasses all frequency ranges used to monitor the structure. A test response to the wideband signal is received at the fixed sensor. The transfer function is created using the test response. The transfer function simulates responses to input signals having frequency ranges encompassed by the selected frequency range.

In another embodiment, the process analyzes the simulated time reversed response by determining whether the simulated time reversed response at the original transmitter matches the original transmitted signal and generates a warning indictor if a match between the received response and the simulated time reversed response is absent.

In another embodiment, the original transmitted signal is sent into a first portion of the structure and the fixed sensor is a first sensor associated with a first transducer in an array of transducers. A second signal having a second frequency range is sent into a second portion of the structure from a second fixed transmitter associated with the second portion of the structure. A second response to the second signal is received at a second fixed sensor associated with the second portion of the structure to form a second received response. The second fixed sensor is a second transducer in the array of transducers. The second received response is time reversed to form a second reversed response.

The second reversed response is processed using a second transfer function to simulate sending the second time reversed response into the structure by the second fixed transmitter. In response to processing the second time reversed response using the second transfer function, a second simulated time response is generated. The second time simulated time reversed response simulates sending the second time reversed response back into the material to generate a second simulated time reversed response at the second transmitter. In this example, the analysis is performed on both the first time reversed response and the second time reversed response to detect anomalies in the structure.

If a comparison between the simulated time reversed response at the original transmitter and the original transmitted signal indicates an anomaly or other damage is associated with the structure a warning is generated.

In another advantageous embodiment, material is tested using virtual time reversal signal processing. In this embodiment, a signal is sent into the material using a transmitter. The signal has a frequency range that falls within a selected frequency range to form a transmitted signal. An actual response to the transmitted signal is received at a sensor. The actual response is reversed to form a time reversed response. The time reversed response is processed using a functional model. The functional model simulates transmitting the time reversed response back through the material to the transmitter to form a simulated time reversed response. The simulated time reversed response is compared to the actual response to determine if a change has occurred in the material.

Figure 6:
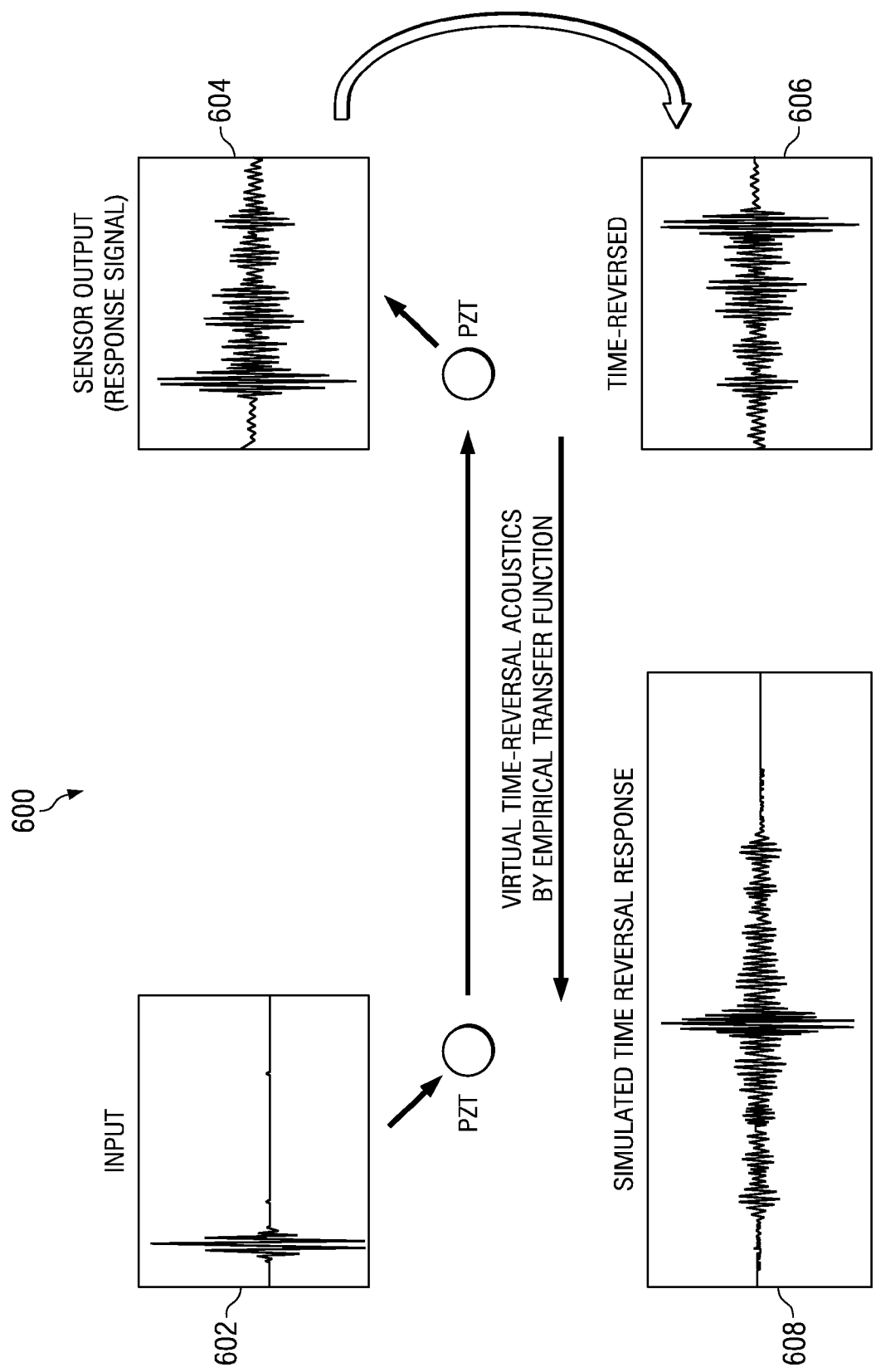
FIG. 6 is a diagram illustrating a virtual time reversal method in accordance with an illustrative embodiment.

FIG. 6 is a diagram illustrating a virtual time reversal method in accordance with an illustrative embodiment. Virtual time reversal process 600 is a process for a virtual time reversal using a functional model to generate a simulated time reversed response rather than using hardware to generate and re-transmit an actual time reversed response.

A transmitter sends input signal 602 for time reversal analysis through a material, such as, without limitation, structure 400 in FIG. 4. The transmitter may also be referred to as an actuator. The input signal is a drive signal, which may also be referred to as a chirp signal, which induces the structure to generate a response signal, such as response 604.

A sensor receives response 604 to input signal 602. In other words, input signal 602 is sent through the material and response 604 is generated as sensor output. The process reverses response 604 to generate time reversed response 606. However, instead of re-transmitting time reversed response 606 back to the original transmitter for time reversal analysis to identify anomalies or damage to the structure, the virtual time reversal process uses time reversed response 606 in a functional model to generate a simulated time reversal response 608.

In other words, the process sends the time reversed response through the functional model to generate a simulated response of the transmitter to receiving the time reversed response without actually transmitting the time reversed response from the sensor to the transmitter. The functional model may also be referred to as a decomposition model. The functional model includes a transfer function that is used to generated simulated time reversal response 608. Simulated time reversal response 608 is generated by the functional model without re-transmitting time reversed response 606 back through the material to the original transmitter.

The functional model simulates the re-transmission of time reversed response 606 through the material and back to the original transmitter. The functional model enables the virtual time reversal process to identify anomalies and damages to the structure using less hardware, fewer transmitters, fewer steps to implement in the structural health monitoring process, and/or less time in performing structural health monitoring.

Figure 7:
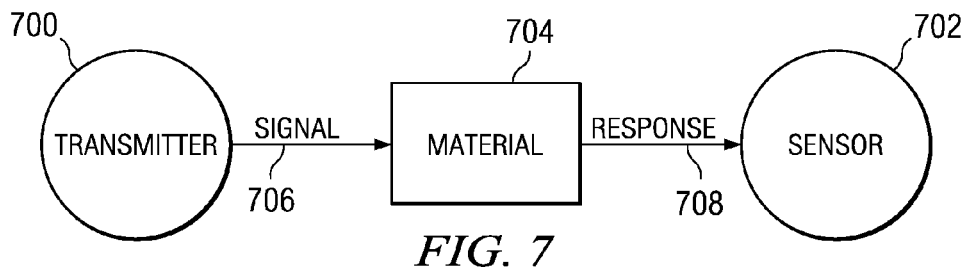
FIG. 7 is a diagram illustrating signal transmission and detection in accordance with an advantageous embodiment.

Turning now to FIG. 7, a diagram illustrating signal transmission and detection is depicted in accordance with an advantageous embodiment. In this example, transmitter 700 and sensor 702 are used to test material 704. Transmitter 700 and sensor 702 are an example of a transmitter and sensor that may be found in transducer system 410 in FIG. 4. Material 704 is an example of a material that is present in a structure, such as fuselage 402 or wings 406 in FIG. 4.

Transmitter 700 transmits or sends signal 706 into material 704. Signal 706 is a waveform having a selected frequency range, such as input signal 602 in FIG. 6. Response 708 is detected by sensor 702.

Response 708 is generated in response to the transmission of signal 706 into material 704. Although, in this example, sensor 702 is shown as receiving response 708 on an opposite side of material 704 from transmitter 700, sensor 702 may be located on the same side of material 704 as transmitter 700. With this configuration, response 708 is detected from reflections or scattering of signal 706 being transmitted into material 704.

Response 708 is used, in these different illustrative examples, in a comparison with a simulated response to determine whether changes have occurred in material 704. These changes may be anomalies that occur through various stresses and other environmental conditions to which material 704 is subjected to over time.

Figure 8:
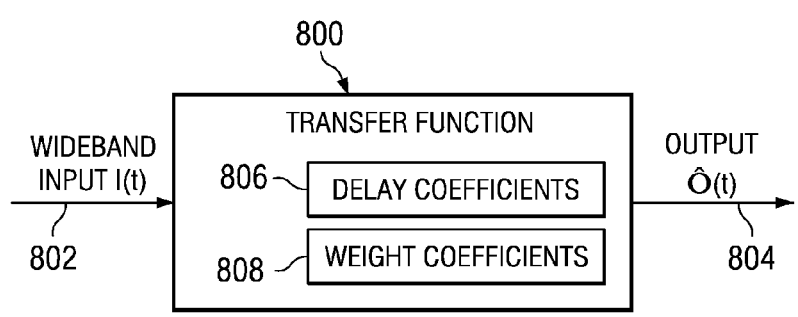
FIG. 8 is a diagram of a functional model in accordance with an advantageous embodiment.

Turning now to FIG. 8, a diagram of a functional model is depicted in accordance with an advantageous embodiment. In this example, transfer function 800 is an example of a component that may be used for functional models 416 in FIG. 4.

Transfer function 800 generates a simulated output in response to an input. In particular, in this example, the input into transfer function 800 is wideband input I(t) 802. Output Ô(t) 804 is a simulated output of the response that would actually be received by a sensor to a particular material as being modeled by transfer function 800. In this example, this output is an approximation and may not be an exact output.

Transfer function 800 contains delay coefficients 806 and weight coefficients 808. These different coefficients of transfer function 800 are determined based on output Ô(t) 804 when wideband input I(t) 802 is input into transfer function 800. In these examples, wideband input I(t) 802 takes the form of a set of parameters. This set of parameters may be one or more parameters that are input into transfer function 800 to generate output Ô(t) 804. In these particular examples, delay coefficients 806 and weight coefficients 808 are identified through empirical testing. The actual response, response 708, detected by sensor 702, in response to signal 706, from transmitter 700 in FIG. 7, is used to create transfer function 800, in these examples.

In these examples, the input is a wideband input that has a frequency range that encompasses all of the different frequency ranges that may be used by the different transmitters for sending signals into one or more structures being monitored by a health monitoring system. In these depicted examples, the frequency range of wideband input I(t) 802 encompasses other frequencies if all of those other frequencies are completely within the frequency range of wideband input I(t) 802. Wideband input I(t) 802 is known and input into transfer function 800.

Delay coefficients 806 and weight coefficients 808 are altered until output Ô(t) 804 matches the output of the actual data for the wideband frequency range. Transfer function 800 may be created as follows:

Given
I(t): input waveform
Ô(t): sensor output data $$\hat{O}(t) = \sum_{i=1}^{N} W_i I_i(t) = \sum_{i=1}^{N} W_i I(t - T_i)$$

where
Ô(t) approximation of O(t)
$T_i$: Delay coefficient
$W_i$: Weight coefficient
$T_i$, $W_i$ will be searched by cross correlation and reducing the residual error As a result, any transmissions by those two transmitters being received may be detected by the sensor and may be modeled using transfer function 800.

In one embodiment, transfer function 800 is a functional model that has a frequency range that encompasses a frequency range of narrowband input. As a result, a simulated response, such as simulated time reversal response 608 in FIG. 6 may be generated to simulate the response that the sensor would perceive from the transmitter. In this example, transfer function 800 is created for a particular transmitter and sensor.

Consequently, if the same sensor receives or detects signals from a different transmitter, then another transmitter function is required. Of course, the wideband input into the transfer function may be from two transmitters and perceived by a single sensor. In other words, if an array of transducers includes three transmitters, there are nine possible paths through the transducers. Therefore, nine transfer functions would be generated for each path through the transducers.

Figure 9:
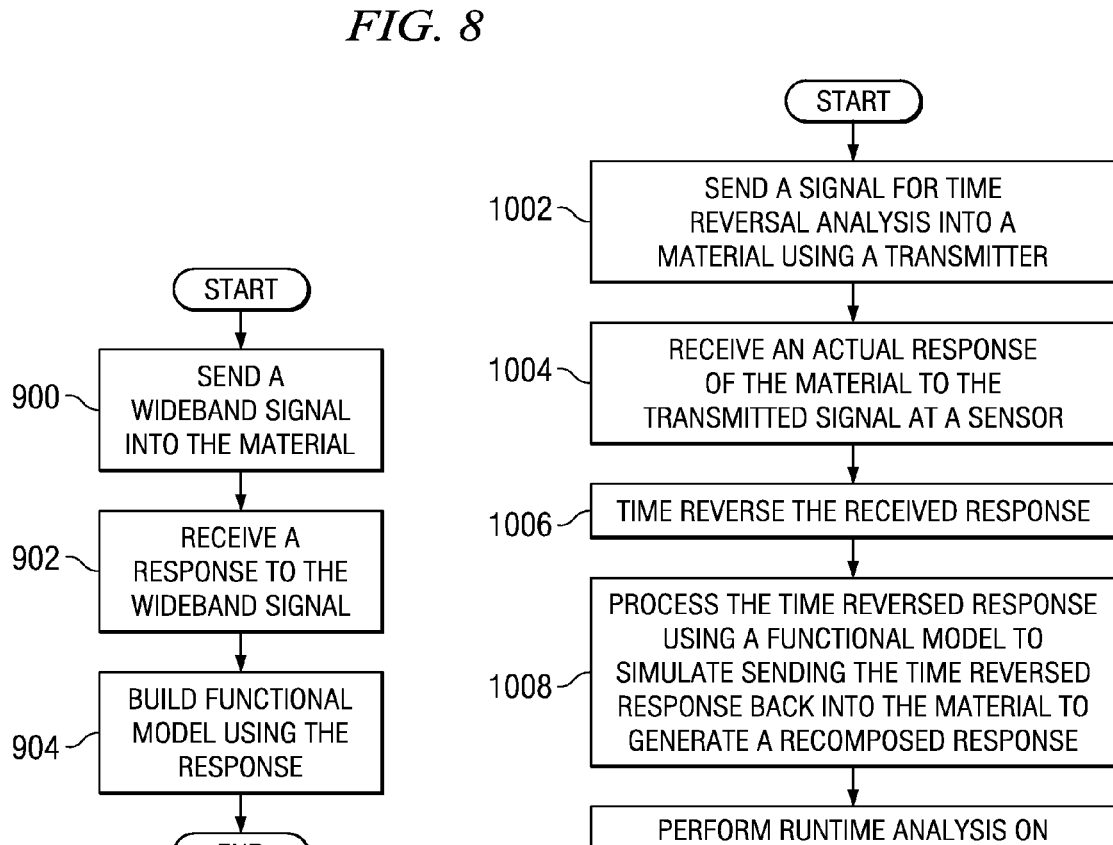
FIG. 9 is a flowchart of a process for building a functional model in accordance with an advantageous embodiment.

Turning now to FIG. 9, a flowchart of a process for building a functional model is depicted in accordance with an advantageous embodiment. In these examples, the process may be implemented in a data processing system, such as data processing system 300 in FIG. 3. The process may be executed before the structural health monitoring system is created or may be processed in the structural health monitoring system that is initially run to create the functional models. The functional models, in these examples, take the form of transfer functions. The functional model can significantly reduce the amount of data storage required by a structural health monitoring system since the transfer function used can reproduce any signal responses within the frequency band used for creating the transfer function.

The process begins by sending a wideband signal into the material (operation 900). This wideband signal has a selected frequency range that encompasses all frequency ranges that may be used in monitoring the material. Next, a response is received to the wideband signal (operation 902).

The functional model is then built using the response (operation 904) with the process terminating thereafter. This functional model is one that is capable of modeling responses to the material at different frequency ranges falling in the selected frequency range for the wideband signals sent into the material in operation 900.

Figure 10:
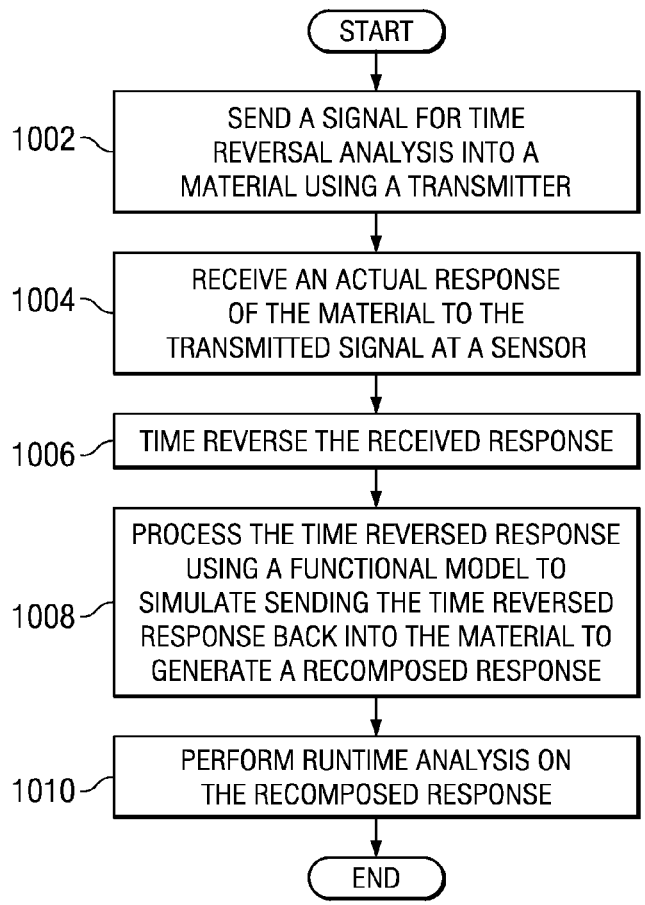
FIG. 10 is a flowchart of a process for using virtual time reversal acoustics to monitor a structure in accordance with an advantageous embodiment.

Turning now to FIG. 10, a flowchart of a process for using virtual time reversal acoustics to monitor a structure is depicted in accordance with an advantageous embodiment. The process illustrated in FIG. 10 may be implemented in a structural health monitoring system, such as structural health monitoring system 408 in FIG. 4.

The structural health monitoring system sends a signal for time reversal analysis into a material using a transmitter (operation 1002). The signal has a frequency range that falls within a selected frequency range to form a transmitted signal, in these examples. Next, an actual response of the material to the transmitted signal is received at a sensor (operation 1004). The structural health monitoring system time reverses the received response (step 1006).

The structural health monitoring system processes the time reversed response using a functional model to simulate sending the time reversed response back into the material to generate a simulated recomposed response (operation 1008). The structural health monitoring system then performs runtime analysis on the simulated recomposed response to determine if a change has occurred in the material (operation 1010) with the process terminating thereafter. If a change has occurred, the change could indicate an anomaly, such as damage, corrosion, degradation, de-lamination in composites, cracking, weakened areas associated with the material, or any other damage.

Thus, the different advantageous embodiments provide a method, apparatus, and computer program product for monitoring structures in a vehicle. In one embodiment, a signal having a frequency range is transmitted into a structure from a fixed transmitter associated with the structure. A response to the signal is received at a fixed sensor associated with the structure to form a received response. The received response is time reversed to form a time reversed response. The time reversed response is processed using a transfer function to simulate sending the time reversed response into the structure by the fixed transmitter. In response to processing the time reversed response using the transfer function, a simulated response that simulates sending the second time reversed response back into the material to generate a simulated time reversed response. A runtime analysis is performed on the simulated time reversed response.

Virtual time reversal is not negatively impacted by environmental conditions because the time reversed signal is processed in a functional model that simulates transmission of the time reversed signal back through the material to the original transmitter. Therefore, temperature variations and other environmental changes that can influence signal transmission and detection do not negatively impact the virtual time reversal signal processing of the illustrative embodiments. Moreover, virtual time reversal requires less hardware to transmit and receive signal because the functional model simulates transmission of the time reversed signal rather than relying on physical hardware to transmit and receive the signals. Thus, the illustrative embodiments allow users to perform virtual time reversal analysis using less physical equipment, less expense, fewer steps, and/or less time than conventional time reversal methods.

The flowcharts and block diagrams in the different depicted embodiments illustrate the architecture, functionality, and operation of some possible implementations of apparatus, methods and computer program products. In this regard, each block in the flowchart or block diagrams may represent a module, segment, or portion of computer usable or readable program code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

The description of the different advantageous embodiments has been presented for purposes of illustration and description, and is not intended to be exhaustive or limited to the disclosure in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the disclosure, the practical application, and to enable others of ordinary skill in the art to understand the disclosure for various embodiments with various modifications as are suited to the particular use contemplated.

What is claimed is:

1. A method for monitoring structures using virtual time reversal signal processing, the method comprising:
    sending a signal having a frequency range into a structure in a vehicle from a fixed transmitter associated with the structure to form an original transmitted signal;
    receiving a response to the original transmitted signal at a fixed sensor associated with the structure to form a received response;
    reversing the received response to form a reversed response;
    processing the reversed response using a transfer function that includes one or more first delay coefficients and one or more first weight coefficients empirically derived for the fixed sensor and for a plurality of fixed transmitters including the fixed transmitter to simulate propagation of the reversed response from the fixed sensor to the fixed transmitter to form a simulated time reversed response, wherein the simulated time reversed response is a simulation of a response of the fixed transmitter to receiving the reversed response from the fixed sensor; and
    performing an analysis on the simulated time reversed response to monitor for anomalies associated with the structure.

2. The method of claim 1 further comprising:
    sending a wideband signal into the structure, wherein the wideband signal has a selected frequency range that encompasses all frequency ranges used to monitor the structure;
    receiving a test response to the wideband signal at the fixed sensor; and
    creating the transfer function using the test response, wherein the transfer function simulates responses to input signals having frequency ranges encompassed by the selected frequency range.

3. The method of claim 1 further comprising:
    determining whether the simulated time reversed response at the original transmitter matches the original transmitted signal; and
    generating a warning indictor if a match between the received response and the simulated time reversed response is absent.

4. The method of claim 1 wherein the original transmitted signal is sent into a first portion of the structure and wherein the fixed sensor is a first sensor associated with a first transducer in an array of transducers, and further comprising:
    sending a second signal having a second frequency range into a second portion of the structure from a second fixed transmitter associated with the second portion of the structure;
    receiving a second response to the second signal at a second fixed sensor associated with the second portion of the structure to form a second received response, wherein the second fixed sensor is a second transducer in the array of transducers;
    time reversing the second received response to form a second reversed response;
    processing the second reversed response using a second transfer function that includes one or more second delay coefficients and one or more second weight coefficients empirically derived for the second fixed sensor and for a plurality of fixed transmitters including the second fixed transmitter to simulate sending the second time reversed response into the structure by the second fixed transmitter; and responsive to processing the second time reversed response using the second transfer function, receiving a second simulated response that simulates sending the second time reversed response back into the material to generate a second simulated time reversed response at the second transmitter.

5. The method of claim 4 further comprising:
performing a runtime analysis on the first time reversed response and the second time reversed response to detect anomalies in the structure.

6. The method of claim 1 further comprising:
generating a warning indicator if a comparison between the simulated time reversed response at the original transmitter and the original transmitted signal indicates an anomaly or other damage is associated with the structure.

7. The method of claim 1 wherein the structure is a structure associated with a vehicle, and wherein the vehicle is one of an aircraft, a car, a tank, a ship, a submarine, or a spacecraft.

8. A method for testing a material using virtual time reversal signal processing, the method comprising:
sending a signal into the material using a transmitter wherein the signal has a frequency range that falls within a selected frequency range to form an original transmitted signal;
receiving an actual response to the transmitted signal at a sensor;
reversing the actual response to form a time reversed response;
processing the time reversed response using a functional model that includes one or more delay coefficients and one or more weight coefficients empirically derived for the sensor and for a plurality of transmitters including the transmitter, wherein the functional model simulates transmitting the time reversed response from the sensor back through the material to the transmitter to form a simulated time reversed response; and
comparing the simulated time reversed response to the original transmitted signal to determine if a change has occurred in the material.

9. The method of claim 8 further comprising:
sending a wideband signal having the selected frequency range into the material using a transmitter;
receiving a response to the signal at the sensor to form a test response; and
building the functional model using the test response, wherein the functional model models transmission of time reversed signals through the material.

10. The method of claim 8 wherein the functional model generates the simulated time reversed response of the material to different frequency ranges falling within a selected frequency range.

11. A structural health monitoring system, the system comprising:
a structure having a plurality of components;
a set of transmitters physically associated with the plurality of components, wherein the set of transmitters send signals into the plurality of components;
a set of sensors physically associated with the plurality of components, wherein the set of transmitters detect responses to the signals;
a transmitter in the set of transmitters, wherein the transmitter sends a signal into a component in the plurality of components, wherein the signal has a frequency range that falls within a selected frequency range to form a transmitted signal;
a sensor in the set of sensors, wherein the sensor receives an actual response to the transmitted signal, generate a simulated time reversed response of the component to the transmitted signal using a functional model that includes one or more delay coefficients and one or more weight coefficients empirically derived for the sensor and for the set of transmitters, wherein the functional model simulates a response of the component to a time reversed signal to form the simulated time reversed response;
an analysis server, wherein the analysis server performs an analysis on the simulated time reversed response to determine if a change has occurred in the material.

12. The system of claim 11, wherein the set of transmitters and the set of sensors are a set of transducers.

13. The system of claim 11, wherein the structure is one of an aircraft, a car, a tank, a ship, a submarine, a spacecraft, a dam, a building, or a bridge.

14. The system of claim 11, wherein the set of transmitters and the set of sensors are physically associated with the plurality of components by being attached to the plurality of components.

15. The system of claim 11, wherein the set of transmitters and the set of sensors are physically associated with the plurality of components by being located within the plurality of components.

16. The system of claim 11 further comprising:
a data processing system executing computer usable program code for the structural health monitoring system, wherein the structural health monitoring system is in communication with the set of transmitters and the set of sensors.

17. A computer program product comprising:
a computer usable storage device having computer usable program code for monitoring structures using virtual time reversal signal processing encoded thereon, the computer usable program code comprising:
computer usable program code for sending a signal having a frequency range into a structure in a vehicle from a fixed transmitter associated with the structure to form an original transmitted response;
computer usable program code for receiving a response to the signal at a fixed sensor associated with the structure to form a received response;
computer usable program code for reversing the received response to form a reversed response;
computer usable program code for processing the reversed response using a transfer function to simulate propagation of the reversed response from the fixed sensor to the fixed transmitter to form a simulated time reversed response, wherein the simulated time reversed response is a simulation of a response of the fixed transmitter to receiving the reversed response from the fixed sensor and wherein the transfer function includes one or more first delay coefficients and one or more first weight coefficients empirically derived for the fixed sensor and for a plurality of fixed transmitters including the fixed transmitter; and
computer usable program code for performing an analysis on the simulated time reversed response to monitor for anomalies associated with the structure.

18. The computer program product of claim 17 further comprising:
- computer usable program code for sending a wideband signal into the structure, wherein the wideband signal has a selected frequency range that encompasses all frequency ranges used to monitor the structure;
- computer usable program code for receiving a test response to the wideband signal at the fixed sensor; and
- computer usable program code for creating the transfer function using the test response, wherein the transfer function simulates responses to input signals having frequency ranges encompassed by the selected frequency range.

19. The computer program product of claim 17 further comprising:
- computer usable program code for determining whether the original transmitted signal matches the simulated time reversed response; and
- computer usable program code for generating a warning indictor if a match between the original transmitted signal and the simulated time reversed response is absent.

20. The computer program product of claim 17 wherein the original transmitted signal is sent into a first portion of the structure and wherein the fixed sensor is a first sensor associated with a first transducer in an array of transducers, and further comprising:
- computer usable program code for sending a second signal having a second frequency range into a second portion of the structure from a second fixed transmitter associated with the second portion of the structure;
- computer usable program code for receiving a second response to the second signal at a second fixed sensor associated with the second portion of the structure to form a second received response, wherein the second fixed sensor is a second transducer in the array of transducers;
- computer usable program code for time reversing the second received response to form a second reversed response;
- computer usable program code for processing the second reversed response using a second transfer function that includes one or more second delay coefficients and one or more second weight coefficients empirically derived for the second fixed sensor and for a plurality of fixed transmitters including the second fixed transmitter to simulate sending the second time reversed response into the structure by the second fixed transmitter; and
- computer usable program code for receiving a second simulated time reversed response in response to processing the second time reversed response using the second transfer function, wherein the second simulated time reversed response simulates sending the second reversed response from the fixed sensor back into the structure to the second fixed transmitter.

21. The computer program product of claim 20 further comprising:
- computer usable program code for performing the analysis on the first time reversed response and the second time reversed response to detect anomalies in the structure.

22. The computer program product of claim 17 further comprising:
- computer usable program code for generating a warning indictor if a comparison between the simulated time reversed response and the original transmitted signal indicates an anomaly or other damage is associated with the structure.

23. The computer program product of claim 17 wherein the structure is a structure associated with a vehicle, and wherein the vehicle is one of an aircraft, a car, a tank, a ship, a submarine, or a spacecraft.

24. A computer program product comprising:
- a computer usable storage device having computer usable program code for testing a material using virtual time reversal signal processing encoded thereon, the computer usable program code configured to be executed by a processor of a computer to perform action comprising:
- sending a signal into the material using a transmitter, wherein the signal has a frequency range that falls within a selected frequency range to form a transmitted signal;
- receiving an actual response to the transmitted signal at a sensor;
- reversing the actual response to form a time reversed response;
- processing the time reversed response using a functional model to form a simulated time reversed response, wherein the functional model includes one or more delay coefficients and one or more weight coefficients empirically derived for the fixed sensor and for a plurality of fixed transmitters including the second fixed transmitter and simulates transmitting the time reversed response back through the material from the sensor to the transmitter; and
- comparing the simulated time reversed response to the original transmitted signal to determine if a change has occurred in the material.

25. The computer program product of claim 24 further comprising:
- sending a wideband signal having the selected frequency range into the material using the transmitter;
- receiving a response to the signal at the sensor; and
- building the functional model, wherein the functional model simulates a response of the transmitter to transmission of time reversed signals from the sensor through the material.

\* \* \* \* \*